(12) United States Patent
Liu et al.

(10) Patent No.: US 11,696,742 B2
(45) Date of Patent: Jul. 11, 2023

(54) ULTRASONIC PROBE WITH CONNECTING BUTT JOINT PORTION, TORQUE TRANSMITTING PORTION, PLUG PORTION, AND SHEATH PORTION

(71) Applicant: Shengsuo Biotech(Shanghai)Corp.Ltd., Shanghai (CN)

(72) Inventors: Changgeng Liu, Shanghai (CN); Hang Yan, Shanghai (CN)

(73) Assignee: Sehngsuo Biotech(Shanghai)Corp. Ltd., Shanghai (CN)

( * ) Notice: Subject to any disclaimer, the term of this patent is extended or adjusted under 35 U.S.C. 154(b) by 309 days.

(21) Appl. No.: 16/611,479

(22) PCT Filed: May 21, 2019

(86) PCT No.: PCT/CN2019/087865
§ 371 (c)(1),
(2) Date: Nov. 7, 2019

(87) PCT Pub. No.: WO2020/228053
PCT Pub. Date: Nov. 19, 2020

(65) Prior Publication Data
US 2021/0290199 A1  Sep. 23, 2021

(30) Foreign Application Priority Data

May 16, 2019  (CN) .......................... 201910409931.X (51) Int. Cl.
*A61B 8/00*  (2006.01)
*A61B 8/12*  (2006.01)
*A61B 1/00*  (2006.01)

(52) U.S. Cl.
CPC ................ *A61B 8/445* (2013.01); *A61B 8/12* (2013.01); *A61B 8/4422* (2013.01);
(Continued)

(58) Field of Classification Search
CPC ......... A61B 8/445; A61B 8/12; A61B 8/4422; A61B 1/00064; A61B 1/00112; A61B 1/00142; A61B 1/00105; A61B 1/00128
See application file for complete search history.

(56) References Cited

U.S. PATENT DOCUMENTS 7,494,467 B2   2/2009  Makin et al.
11,123,521 B2 *  9/2021  Sakaguchi ........ A61M 25/0105
(Continued)

FOREIGN PATENT DOCUMENTS

CN     205494052 U  *  8/2016
CN     107080604 A  *  8/2017   ............... A61F 2/07
(Continued)

*Primary Examiner* — Christopher Koharski
*Assistant Examiner* — Richmond J Van Winter
(74) *Attorney, Agent, or Firm* — JCIP Global Inc.

(57) ABSTRACT

A sheath assembly is adapted for an ultrasonic probe and includes a plug portion and a sheath portion connected to each other. One end of the plug portion of the sheath assembly is used for detachably and fixedly connecting with a connecting butt joint portion of the ultrasonic probe, so that the plug portion and the connecting butt joint portion are detachable after the ultrasonic probe is used. An inside of the plug portion communicates with an inside of the sheath portion to receive a torque transmitting portion of the ultrasonic probe.

6 Claims, 11 Drawing Sheets

(52) U.S. Cl.
CPC ....... *A61B 1/00064* (2013.01); *A61B 1/00112* (2013.01); *A61B 1/00142* (2013.01)

(56) References Cited

U.S. PATENT DOCUMENTS

| | | | |
|---|---|---|---|
| 2018/0055343 A1* | 3/2018 | Yang | A61B 8/4416 |
| 2019/0192116 A1* | 6/2019 | Beckers | A61B 8/445 |
| 2019/0374196 A1* | 12/2019 | Courtney | A61B 5/0075 |

FOREIGN PATENT DOCUMENTS

| | | | | |
|---|---|---|---|---|
| CN | 208481369 U | * | 2/2019 | A61B 8/12 |
| DE | 2759007 A | * | 8/1978 | B23B 31/003 |
| DE | 3525948 A | * | 1/1987 | F16B 39/023 |
| JP | 3409655 B2 | * | 5/2003 | A61B 8/12 |
| WO | WO-9921672 A1 | * | 5/1999 | B23B 31/201 |

* cited by examiner

FIG. 11

ULTRASONIC PROBE WITH CONNECTING BUTT JOINT PORTION, TORQUE TRANSMITTING PORTION, PLUG PORTION, AND SHEATH PORTION

CROSS-REFERENCE TO RELATED APPLICATION

This application is a 371 of international application of PCT application serial no. PCT/CN2019/087865, filed on May 21, 2019, which claims the priority benefit of China application no. 201910409931.X, filed on May 16, 2019. The entirety of each of the above mentioned patent applications is hereby incorporated by reference herein and made a part of this specification.

BACKGROUND

Technical Field

The present invention relates to the technical field of medical instruments, and more specifically, to a sheath assembly, an ultrasonic probe and an assembling method thereof.

Description of Related Art

Ultrasound endoscope is a commonly used medical instrument, and its ultrasonic probe can enter the organ of the human body to be examined through the natural cavity of the human body, such as a urinary tract or a surgical incision, and directly peep into the lesion of the relevant part, to assist in obtaining clear images.

A fiber-optic ultrasound endoscope in an ultrasound endoscope has an elongated ultrasonic probe that allows an ultrasonic transducer attached to one end of the ultrasonic probe to penetrate deep into the human body. In addition, the ultrasonic transducer is connected to the driver of the other end of the ultrasonic probe and the imaging system through a coaxial cable. Driven by an external motor, the ultrasonic transducer may be free to rotate within the ultrasonic probe to create a circular or cross-sectional image of the tissue section perpendicular to the axial direction.

However, most fiber-optic ultrasound endoscopes in the prior art are integral structures. Due to the high cost of ultrasonic transducers, after each clinical application process, the part of the ultrasonic probe that directly contacts the human tissue is cleaned and disinfected, and then continues to be used for the next clinical use, which is prone to cause the problem of cross-infection. Also, the practice of abandoning the entire ultrasonic probe after each clinical application has resulted in a significant increase in treatment costs.

Therefore, it is necessary to develop a new type of ultrasonic probe to avoid the above problems in the prior art.

SUMMARY

It is an object of the invention to provide a sheath assembly, an ultrasonic probe having the sheath assembly, and an assembling method of the ultrasonic probe, so as to avoid the problem of prone to cross infection caused by the overall repetitive use of the ultrasonic probe in the prior art while reducing the cost of treatment.

To achieve the above object, the sheath assembly of the invention comprises a plug portion and a sheath portion, and one end of the plug portion is used for detachably and fixedly connecting with a connecting butt joint portion of the ultrasonic probe. The other end of the plug portion is fixedly connected to one end of the sheath portion, and an inside of the plug portion communicates with an inside of the sheath portion to receive a torque transmitting portion of the ultrasonic probe.

The sheath assembly of the invention has the following beneficial effects: one end of the plug portion is used for detachably and fixedly connecting with a connecting butt joint portion of the ultrasonic probe, so that the plug portion and the connecting butt joint portion are detachable after the ultrasonic probe is used. Therefore, on the one hand, the connecting butt joint portion to which the torque transmitting portion is fixed is retained for subsequent application process to facilitate reducing treatment costs; on the other hand, the used sheath assembly may be directly discarded due to its direct contact with human tissue and low cost, thereby avoiding cross-infection problems caused by repeated use.

Preferably, the plug portion comprises a recess, and an inner sidewall of the recess has a first threaded structure to effect the detachably fixed connection with the connecting butt joint portion through threaded engagement. The beneficial effects include: the detachably fixed connection of the plug portion and the connecting butt joint portion may be quickly achieved by threaded engagement.

Further preferably, a bottom portion of the recess is provided with a first locking portion, and an inside of the first locking portion communicates with an inside of the sheath portion; an outer sidewall of the first locking portion is engageable with an inner sidewall of the connecting butt joint portion such that the first locking portion is received inside the connecting butt joint portion. The beneficial effects include: it is advantageous to further improve the sealing performance between the plug portion and the connecting butt joint portion.

Preferably, the first locking portion has a first inner diameter for receiving the torque transmitting portion, the first inner diameter being greater than or equal to 0.5 mm and larger than an outer diameter of the torque transmitting portion. The beneficial effects include: it is advantageous for the torque transmitting portion to be freely rotatable within the first locking portion to obtain good image information.

Further preferably, the outer sidewall of the first locking portion has a taper such that the first locking portion is received inside the connecting butt joint portion and is fixedly connected to the connecting butt joint portion by taper self-locking.

Further preferably, the taper ranges from 3 degrees to 6 degrees to enable the sheath assembly to withstand at least 1 atmosphere for a period of at least 30 seconds. The beneficial effects include: the strength of the sheath assembly is further increased.

Still more preferably, the plug portion has a sealing portion for detachably and fixedly connecting to the first locking portion. The beneficial effects include: it is advantageous to subsequently inject the liquid into the sheath assembly for sealing to facilitate storage or transport of the sheath assembly.

Preferably, the other end of the sheath portion has a sealing head structure. The beneficial effects include: it is convenient to receive the liquid in the sheath portion during the subsequent use of the ultrasonic probe to facilitate the good signal transmission function of the ultrasonic transducer of the torque transmission portion.

Preferably, the sheath portion has a first sheath and a second sheath that are connected to each other, one end of the first sheath being fixedly connected to the sheath connecting portion of the plug portion, the first sheath having a Shore hardness greater than that of the second sheath. The beneficial effects include: the first sheath connected to the sheath connecting portion has a Shore hardness greater than that of the second sheath at the distal end, which is advantageous for enhancing the strength of the sheath portion and facilitates the sheath portion to be smoothly pushed in the body; on the other hand, the second sheath having a lower Shore hardness directly contacts human tissue, and may reduce damage to human tissues, which also facilitates bending to enter more complicated and narrow channels.

Further preferably, the sheath portion also has a third sheath, and the third sheath has a Shore hardness greater than or equal to that of the first sheath and is at least partially sleeved outside of the first sheath to enhance a strength of the sheath portion. The beneficial effects include: it is convenient for the sheath portion to smoothly carry out the pushing process in the body.

Still more preferably, one end of the third sheath is fixedly connected to the sheath connecting portion, and is sleeved outside of the first sheath, a length of the third sheath is less than that of the first sheath.

Still more preferably, the first sheath has a Shore hardness of 50 D-90 D, the second sheath has a Shore hardness of 30 D-75 D, and the third sheath has a Shore hardness of 50 D-90 D.

Still more preferably, the third sheath is a metal spring sleeve, and the metal spring sleeve is movably sleeved outside of the sheath connecting portion and the outside of a portion of the first sheath.

The ultrasonic probe of the invention comprises a connecting butt joint portion, a torque transmitting portion, and the sheath assembly. The sheath assembly has a plug portion and a sheath portion which are connected to each other. The connecting butt joint portion is detachably and fixedly connected to the plug portion. A fixed end of the torque transmission portion is fixedly connected in the connecting butt joint portion, and a transducer end of the torque transmitting portion extends through the connecting butt joint portion and the plug portion to enter the sheath portion.

The beneficial effects of the ultrasonic probe of the present invention include: the connecting butt joint portion of the ultrasonic probe is detachably and fixedly connected to the plug portion, so that the plug portion and the connecting butt joint portion are detachable after the ultrasonic probe is used. Therefore, on the one hand, the connecting butt joint portion to which the torque transmitting portion is fixed is retained for subsequent application process to facilitate reducing treatment costs; on the other hand, the used sheath assembly may be directly discarded due to its direct contact with human tissue and low cost, thereby avoiding cross-infection problems caused by repeated use.

Preferably, the connecting butt joint portion has a first connecting portion, and the first connecting portion has a second inner diameter. The second inner diameter is used for receiving the torque transmitting portion, and the second inner diameter is greater than or equal to 0.5 mm and is larger than an outer diameter of the torque transmitting portion. The beneficial effects include: it is advantageous for the torque transmitting portion to be freely rotatable within the first connecting portion to obtain good image information.

Further preferably, the connecting butt joint portion further has a second connecting portion, and the second connecting portion is coaxially connected to the first connecting portion detachably and fixedly. A portion of the outer surface of the second connecting portion has a second threaded structure for locking with the plug portion through threaded engagement.

Further preferably, the plug portion has a first locking portion, and the second connecting portion receives the first locking portion such that an inside of the connecting butt joint portion communicates with an inside of the sheath assembly, and an inner sidewall of the second connecting portion is fitted to an outer sidewall of the first locking portion. The beneficial effects include: further improving the sealing performance between the plug portion and the connecting butt joint portion.

Still more preferably, the inner sidewall of the second connecting portion has a taper to receive the first locking portion, and the second connecting portion is connected to the first locking portion by taper self-locking. The beneficial effects include: the strength of the ultrasonic assembly is enhanced on the basis of further improving the sealing performance.

Still more preferably, the first locking portion has the Shore hardness less than that of the second connecting portion. The beneficial effects include: the sealing performance is further enhanced by a combination of softness and hardness.

A method of assembling the ultrasonic probe comprises following steps.

S1: Providing the sheath assembly, a drainage tube and a liquid injection device, the sheath assembly including the plug portion and the sheath portion which are connected to each other; passing one end of the drainage tube into a bottom portion of the sheath portion through the plug portion; and injecting a liquid into the sheath portion through the other end of the drainage tube using the liquid injection device.

S2: Providing the connecting butt joint portion with the torque transmitting portion being fixed thereon, inserting a transducer end of the torque transmitting portion from the plug portion into the sheath portion, and then locking the plug portion to the connecting butt joint portion, so as to complete assembly of the ultrasonic probe.

The method of assembling the ultrasonic probe of the invention has the following beneficial effects: since the assembly of the ultrasonic probe may be completed by locking the plug portion to the connecting butt joint portion, in the subsequent disassembling process, the connecting butt joint portion to which the torque transmitting portion is fixed is retained on the one hand for subsequent application process to facilitate reducing treatment costs, and the used sheath assembly may be directly discarded on the other hand due to its direct contact with human tissue and low cost, thereby avoiding cross-infection problems caused by repeated use.

Preferably, the plug portion is provided with a sealing portion, in the step S1, the sealing portion is removed to inject the liquid into the sheath portion through the drainage tube and the liquid injection device.

Preferably, the method further includes step S3. In the step S3, the connecting butt joint portion and the plug portion are unlocked after the ultrasonic probe is used, the sealing structure of the sheath portion is broken, and the connecting butt joint portion is pulled to pull the torque transmitting portion away from the sheath assembly. The beneficial effects include: after unlocking the connecting butt joint portion and the plug portion, the sealing structure of the sheath portion is broken, so as to pull the connecting butt joint portion to pull the torque transmitting portion away from the sheath assembly.

Further preferably, a distal end of the sheath portion has a sealing head structure, and in the step S3, after the connecting butt joint portion and the plug portion are unlocked, the sealing head structure is cut to break the sealing structure of the sheath portion.

Further preferably, in the step S3, after the connecting butt joint portion and the plug portion are unlocked, an outer sidewall of the sheath portion is destroyed to break the sealing structure of the sheath portion.

DESCRIPTION OF THE EMBODIMENTS

In order to make objectives, technical solutions, and advantages of the present invention clearer, the technical solutions in the present invention are described clearly and completely in the following with reference to accompanying drawings in the embodiments of the present invention. Apparently, the described embodiments are only part rather than all of the embodiments of the present invention. Based on the embodiments of the present invention, all the other embodiments obtained by those of ordinary skill in the art without inventive effort are within the scope of the present invention. Unless otherwise mentioned, all technical and scientific terms used herein have the same meaning as commonly understood by one of ordinary skill in the art to which the invention belong. "Comprise", "include" and the like are intended to denote the element or object before the word is included in the listed element or object and thereof equivalents after the word, instead of excluding other elements or objects.

In view of the problems existing in the prior art, embodiments of the present invention provide a sheath assembly and a method of preparing the sheath assembly. The sheath assembly is adapted for an ultrasonic probe.

The sheath assembly has a plug portion and a sheath portion. A proximal end of the sheath portion is fixedly connected to the sheath connecting portion of the plug portion, and the proximal end is defined as an end adjacent to the plug portion. One end of the plug portion is used for detachably and fixedly connecting with a connecting butt joint portion of the ultrasonic probe. The sheath connecting portion is fixedly connected to one end of the sheath portion, and the inside of the plug portion communicates with the inside of the sheath portion to receive a torque transmitting portion of the ultrasonic probe.

In some embodiments of the present invention, at least a portion of the outer surface of the sheath portion is hydrophilic.

The preparation method for the sheath assembly comprises:

Providing the plug portion and the sheath portion to be processed, and performing a head sealing treatment on one end of the sheath portion to be processed to form a sealing head structure.

Performing a hydrophilic treatment on at least a portion of the outer surface of the sheath portion to be processed to form the sheath portion.

Connecting an opening end of the sheath portion fixedly to the sheath connecting portion of the plug portion to form the sheath assembly.

In some embodiments of the present invention, a hydrophilic treatment is performed on the at least a portion of the outer surface of the sheath portion to be processed in a radial direction of the sheath portion to be processed from a distal end point of the sealing head structure as a starting point to form the sheath portion.

In some embodiments of the present invention, the region of the outer surface of the sheath portion to be processed that needs the hydrophilic treatment comprises a region directly in contact with human tissue to enhance biocompatibility of the sheath portion.

Embodiments of the present invention further provide an ultrasonic probe, and an assembling method of the ultrasonic probe.

The ultrasonic probe comprises the sheath assembly, the connecting butt joint portion, and the torque transmitting portion. A transducer end of the torque transmitting portion is fixed with an ultrasonic transducer with the other end of the ultrasonic transducer being a fixed end. The fixed end is fixedly connected inside the connecting butt joint portion. The connecting butt joint portion is connected to the plug portion in a detachably fixed connection, and a transducer end of the torque transmitting portion extends through the connecting butt joint portion and the plug portion to enter the sheath portion.

The method of assembling the ultrasonic probe comprises:

S1: Providing the sheath assembly, a drainage tube and a liquid injection device, the sheath assembly including the plug portion and the sheath portion which are connected to each other; passing one end of the drainage tube into a bottom portion of the sheath portion through the plug portion; and injecting a liquid into the sheath portion through the other end of the drainage tube using the liquid injection device.

S2: Providing the connecting butt joint portion to which the torque transmitting portion is fixed, inserting a transducer end of the torque transmitting portion from the plug portion into the sheath portion, and then locking the plug portion to the connecting butt joint portion, so as to complete assembly of the ultrasonic probe.

In some embodiments of the present invention, a sealing portion is used to seal the plug portion to seal the liquid inside the sheath assembly and facilitate the transportation of the sheath assembly.

In the step S1 of some embodiments of the present invention, the plug portion is provided with a sealing portion and the sealing portion is removed to inject the liquid into the sheath portion.

In some embodiments of the present invention, the connecting butt joint portion and the plug portion are unlocked after using the ultrasonic probe, the sealing structure of the sheath portion is broken, and the connecting butt joint portion is pulled to pull the torque transmitting portion away from the sheath assembly.

In some embodiments of the present invention, a distal end of the sheath portion has a sealing head structure, and the sealing head structure is cut to break the sealing structure of the sheath portion.

In some embodiments of the present invention, an outer sidewall of the sheath portion is destroyed to break the sealing structure of the sheath portion. Specifically, the sealing structure of the sheath portion is broken by opening a through hole in the outer sidewall of the sheath portion or slashing the outer sidewall of the sheath portion.

The technical solutions of the present invention will be described in detail below by way of Embodiments 1-6.

Embodiment 1

The present embodiment provides a first sheath assembly having a first plug portion and a sheath portion.

Figure 1:
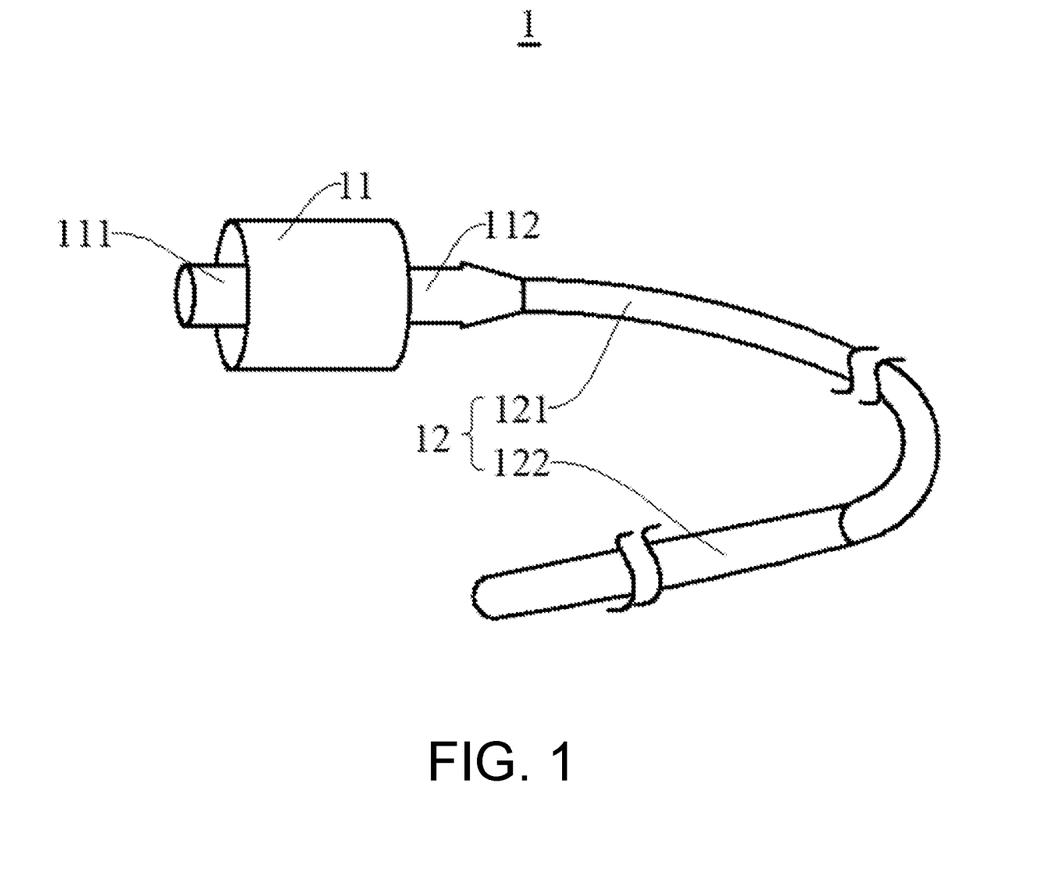
FIG. 1 is a structural view of a first sheath assembly of Embodiment 1 of the present invention.
Figure 2:
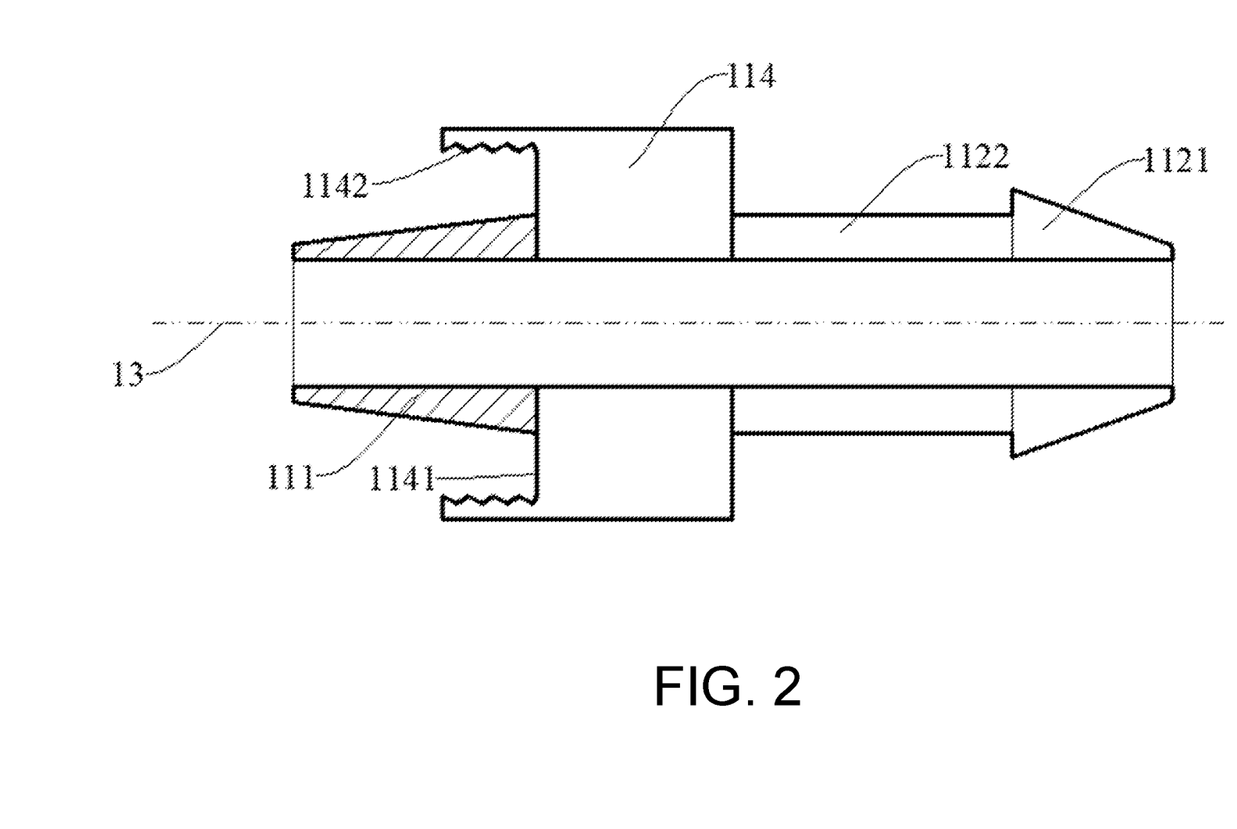
FIG. 2 is a longitudinal sectional view of a plug portion shown in FIG. 1.

FIG. 1 is a structural view of a first sheath assembly of Embodiment 1 of the present invention. FIG. 2 is a longitudinal sectional view of a first plug portion shown in FIG. 1.

With reference to FIGS. 1 and 2, the first sheath assembly 1 has a first plug portion 11 and a sheath portion 12. The first plug portion 11 has a first locking portion 111 and a first sheath connecting portion 112. The sheath portion 12 has a first sheath 121 and a second sheath 122.

With reference to FIGS. 1 and 2, the first plug portion 11 has a cylindrical fixing portion 114. One end of the fixing portion 114 defines a first recess 1141, and the first recess 1141 is a cylindrical recess. The first locking portion 111 has an internal hollow structure, and a passage inside the fixing portion 114 communicates with the inside of the first sheath connecting portion 112 to receive a torque transmitting portion (not shown). One end of the first locking portion 111 is fixed to a bottom portion of the first recess 1141. The first sheath connecting portion 112 is a hollow structure having an extension tube 1122 and a conical joint tube 1121 which are sequentially connected. One end of the extension tube 1122 is fixed to the other end of the fixing portion 114, and the conical joint tube 1121 is fixedly connected to one end of the first sheath 121. A center line of the first locking portion 111 and a center line of the first sheath connecting portion 112 both coincide with a center line 13 of the fixing portion 114.

With reference to FIGS. 1 and 2, the first locking portion 111 is a truncated cone structure, and the longitudinal cross-sectional shape thereof is an isosceles trapezoid. That is, the outer sidewall of the first locking portion 111 has a taper shape so as to be received inside the connecting butt joint portion (not shown), and is fixedly connected with the connecting butt joint portion (not shown) by taper self-locking. The manner of taper self-locking is advantageous to enhance the sealability and strength of the ultrasonic probe assembled by the sheath assembly 1. When the sheath assembly 1 is injected with liquid and assembled into the ultrasonic probe, the sheath assembly 1 may withstand at least 1 atmosphere for at least 30 seconds without causing the liquid leakage. The taper is a ratio between an absolute value of a difference between the lengths of the two base sides of the isosceles trapezoid and a height of the isosceles trapezoid.

In some specific embodiments of the present invention, the taper ranges from 3 degrees to 6 degrees. The sheath assembly 1 may withstand at least 3 atmospheres for at least 30 seconds without causing the liquid leakage.

With reference to FIGS. 1 and 2, the first sheath 121 is a hollow tube structure with two open ends, with one end being fixed to the inner wall of a tapered joint of the first sheath connecting portion 112 by an epoxy resin glue, and the other end being fixed to one end of the second sheath 122 by heat fusion. The distal end of the second sheath 122 is a hemispherical sealing head structure. The inner sidewall of the first recess 1141 has a first threaded structure 1142.

In some embodiments of the present invention, the first locking portion 111 has a first inner diameter that is greater than or equal to 0.5 mm and larger than an outer diameter of the torque transmitting portion for receiving the torque transmitting portion. In some specific embodiments of the present invention, the first inner diameter is any one of 0.5 mm, 1.0 mm, 1.2 mm, and 1.4 mm.

In the present embodiment, the first sheath 121 and the second sheath 122 have the same inner diameter and the same outer diameter. A length of the first sheath 121 is greater than a length of the second sheath 122. In some specific embodiments of the present invention, the length of the first sheath 121 is 175 cm, and the length of the second sheath 122 is 5 cm.

In some embodiments of the present invention, with reference to FIG. 2, the sheath portion 12 has only the second sheath 122, and one end of the second sheath 122 is fixedly connected to the conical joint tube 1121.

In some embodiments of the present invention, the second sheath 122 is a hollow tube structure with two open ends, that is, the distal end of the second sheath 122 does not have the sealing head structure.

In some embodiments of the present invention, the constituent materials of the first sheath 121 and the second sheath 122 are both plastic. In some specific embodiments of the present invention, the constituent material of the plastic is polyetheramide elastomer, high density polyethylene or nylon.

In the present embodiment, with reference to FIGS. 1 and 2, the Shore hardness of the first sheath 121 is greater than the Shore hardness of the second sheath 122. The first sheath 121 has a Shore hardness of 75 D and the second sheath 122 has a Shore hardness of 50 D. On the one hand, the first sheath 121 connected to the first sheath connecting portion 112 has a Shore hardness greater than that of the second sheath 122, which is advantageous for enhancing the strength of the sheath portion 12 and facilitates the sheath portion 12 to be smoothly pushed in the body. On the other hand, the second sheath 122 having a lower Shore hardness directly contacts human tissue, which may reduce damage to the human tissue.

In some embodiments of the present invention, the first sheath 121 has a Shore hardness of 50 D-90 D and the second sheath 122 has a Shore hardness of 30 D-75 D. In some specific embodiments of the present invention, the first sheath 121 has a Shore hardness of any one of 60 D, 70 D, 75 D, 80 D, and 85 D, and the second sheath 122 has a Shore hardness of any one of 30 D, 40 D, 45 D, 55 D, 60 D, 65 D, 70 D, and 75 D.

With reference to FIG. 1, starting from an end point of the sealing head structure of the second sheath 122, a hydrophilic treatment is performed along the radial direction of the sheath portion 12 to form a hydrophilic modification layer on at least a portion of the surface of the sheath portion 12.

A liquid is injected into the sheath portion using a liquid injection device containing the liquid therein. The liquid injection device has an injection syringe and a drainage tube, and the inside of the injection syringe is filled with the liquid. With reference to FIGS. 1 and 2, the drainage tube (not shown) is inserted into the sheath portion 12 via the first locking portion 111, and one end of the drainage tube (not shown) is caused to reach a bottom portion of the second sheath portion 122 with the other end of the drainage tube extending beyond the first locking portion 111. The injection syringe (not shown) is inserted into the drainage tube (not shown), followed by slowly injecting the liquid into the sheath portion 12, and the drainage tube (not shown) is slowly pulled out of the first locking portion 111 through the injection syringe (not shown) while injecting the liquid, so as to ensure that no air bubbles are generated inside the sheath portion 12. After the injection of the liquid in the syringe (not shown) is completed, the drainage tube (not shown) is withdrawn, and the first locking portion 111 is then sealed using a sealing portion (not shown).

In the present embodiment, an outer diameter of the drainage tube is smaller than the inner diameter of the first locking portion 111 and smaller than the inner diameter of the sheath portion 12, and the constituent material of the drainage tube is plastic.

In some embodiments of the present invention, the liquid injected into the sheath portion is at least capable of immersing the ultrasonic transducer of the torque transmitting portion to facilitate signal transmission of the ultrasonic transducer to obtain a clear image.

In some embodiments of the present invention, the liquid is any one of physiological saline or silicone oil. The plastic is Polyetheretherketone (PEEK).

Embodiment 2

The present embodiment provides a second sheath assembly which differs from the first sheath assembly of Embodiment 1 of the present invention in that the sheath portion further has a third sheath, which is a hollow tube.

Figure 3:
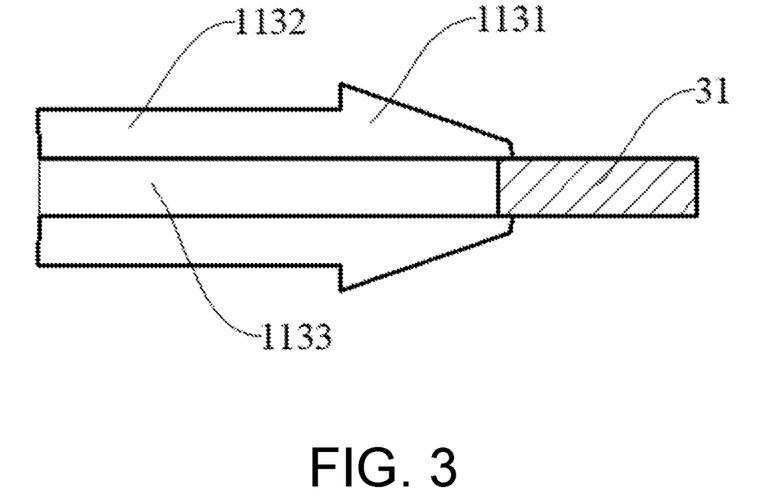
FIG. 3 is a view showing the assembly of a third sheath and a sheath connecting portion in Embodiment 2 of the present invention.

FIG. 3 is a view showing the assembly of a third sheath and a sheath connecting portion in the embodiment. With reference to FIGS. 1 to 3, the outer diameter of a hollow tube 31 is adapted to the diameter of a hollow duct 1133 inside the first sheath connecting portion 112. One end of the hollow tube 31 extends to the inside of the hollow duct 1133, and is adhered and fixed to the inner wall of the conical joint tube 1121 by epoxy glue to be sleeved outside the first sheath 121. One end of the first sheath 121 is fixed to the inner wall of the first sheath connecting portion 112 by epoxy glue or heat fusion. The length of the hollow tube 31 is smaller than that of the first sheath 121.

In some embodiments of the present invention, the outer diameter of the first sheath 121 is adapted to the inner diameter of the hollow tube 31.

In the present embodiment, the Shore hardness of the hollow tube 31 is greater than or equal to that of the first sheath 121. The Shore hardness of the hollow tube 31 is 50 D to 90 D. In some specific embodiments of the present invention, the third sheath has a Shore hardness of any one of 50 D, 60 D, 65 D, 70 D, 75 D, and 80 D.

Embodiment 3

The present embodiment provides a third sheath assembly. The third sheath assembly differs from the second sheath assembly of Embodiment 2 of the present invention in that the third sheath is a metal spring sleeve. The metal spring sleeve is movably sleeved outside the sheath connecting portion and a portion of the first sheath to enhance a connection relationship between the sheath connecting portion and the sheath portion.

Figure 4:
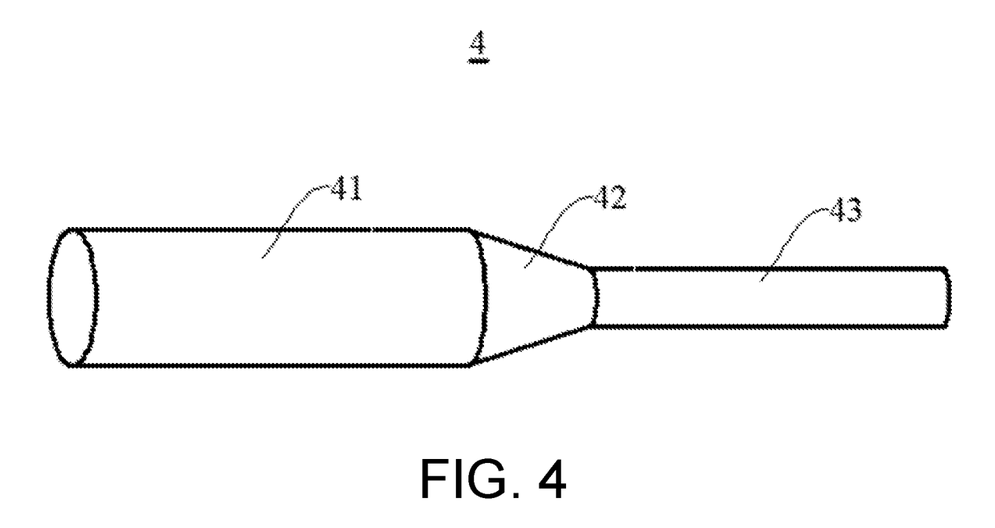
FIG. 4 is a structural view of a spring sleeve of Embodiment 3 of the present invention.

FIG. 4 is a structural view of a metal spring sleeve of Embodiment 3. With reference to FIGS. 2, 3 and 4, a metal spring sleeve 4 has a first sleeve 41, a tapered sleeve 42, and a second sleeve 43 which are sequentially connected. A length of the first sleeve 41 is equal to a length of the extension tube 1122, and an inner diameter thereof is adapted to the outer diameter of the extension tube 1122. A length of the tapered sleeve 42 is equal to the length of the conical joint tube 1121, and the shape of the inner wall thereof is the same as the shape of the outer wall of the conical joint tube 1121. A length of the second sleeve 43 is smaller than the length of the first sheath 121, and an inner diameter of the second sleeve 43 is adapted to the outer diameter of the third sheath 31. The metal spring sleeve 4 is a movable sleeve that is movable in the radial direction of the first sheath 121.

Embodiment 4

The present embodiment provides a fourth sheath assembly. The fourth sheath assembly differs from the third sheath assembly of Embodiment 3 of the present invention in that the fourth sheath assembly further has a sealing portion which is a sealing sleeve head.

Figure 5A:
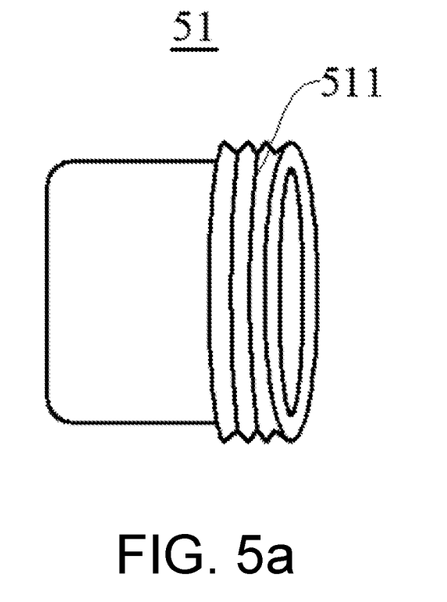
FIG. 5a is a structural view of a sealing sleeve head of Embodiment 4 of the present invention.

FIG. 5a is a structural view of a sealing sleeve head of Embodiment 4. With reference to FIGS. 2 and 5a, the first sealing sleeve 51 is a hollow structure that is open at one end. The outer sidewall of the first sealing sleeve head 51 has a first locking thread 511 for engaging the first threaded structure 1142. The inner sidewall of the first sealing sleeve head 51 has a taper to receive the first locking portion 111, so that the outer sidewall of the first locking portion 111 is fitted to the inner sidewall of the first sealing sleeve head 51 in a self-locking manner. A bottom portion of the first sealing sleeve head 51 is fitted to the end surface of the first locking portion 111 to seal the first locking portion 111.

Figure 5B:
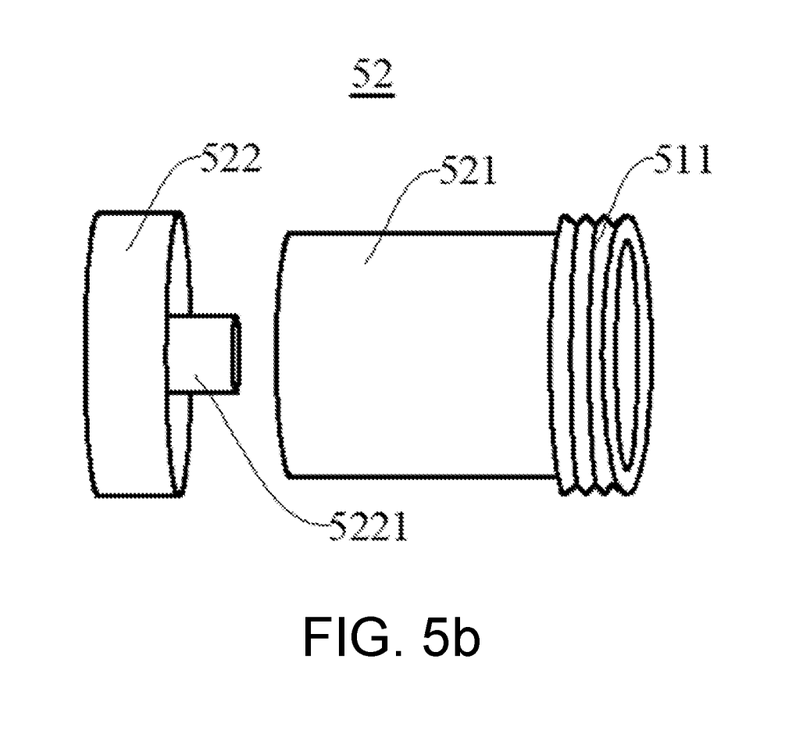
FIG. 5b is an exploded view of another sealing sleeve head of Embodiment 4 of the present invention.

FIG. 5b is an exploded view of another type of sealing sleeve head of Embodiment 4. With reference to FIGS. 2 and 5b, a second sealing sleeve head 52 has a sealing tube 521 and a sealing head 522. The sealing plug 522 is a cylindrical structure having an intermediate recess (not shown) at one end. A bottom portion of the intermediate recess (not shown) has a plug 5221.

The sealing tube 521 is a hollow structure that is open at both ends. A portion of the outer sidewall of one end of the sealing tube 521 has the first locking thread 511, and a portion of the inner sidewall thereof has a taper, so as to receive the first locking portion 111, so that the outer sidewall of the first locking portion 111 is fitted to a portion of an inner sidewall of the second sealing sleeve head 52 in a taper self-locking manner. Another portion of the inner sidewall of the sealing tube 521 is used for receiving the plug 5221, and the inner sidewall of the intermediate recess (not shown) is engaged with a portion of the outer sidewall of the sealing tube 521, so that the sealing head 522 is detachably and fixedly connected to the sealing tube 521.

Embodiment 5

The present embodiment provides a first ultrasonic probe comprising the first sheath assembly 1, the connecting butt joint portion 60, and the torque transmitting portion 9. The connecting butt joint portion 60 has a first connecting portion 61 and a second connecting portion 62, and the first connecting portion 61 is coaxially connected to the second connecting portion 62 detachably and fixedly. The second connecting portion 62 is detachably and fixedly connected to the first sheath assembly 1.

In some embodiments of the present invention, the first connecting portion and the second connecting portion realize a coaxial connection in a manner of concave-convex abutting and pin fixing.

In some embodiments of the present invention, the constituent material of the connecting butt joint portion is metal, and the constituent material of the plug portion is a polymer. In some specific embodiments of the present invention, the constituent material of the connecting butt joint portion is stainless steel or copper, and the constituent material of the plug portion is a polypropylene.

In some specific embodiments of the present invention, the first ultrasonic probe has a metal outer sleeve that is sleeved on the outer surface of the connecting butt joint portion, and the outer surface of the connecting butt joint portion is fitted to the inner surface of the metal outer sleeve, which is advantageous for enhancing the signal transmission effect of the torque transmitting portion.

In some specific embodiments of the present invention, the first ultrasonic probe further has an insulating outer sleeve sleeved on the outside of the metal sleeve to increase surface friction, and the inner surface of the insulating outer sleeve is fitted to the outer surface of the metal sleeve.

Figure 6:
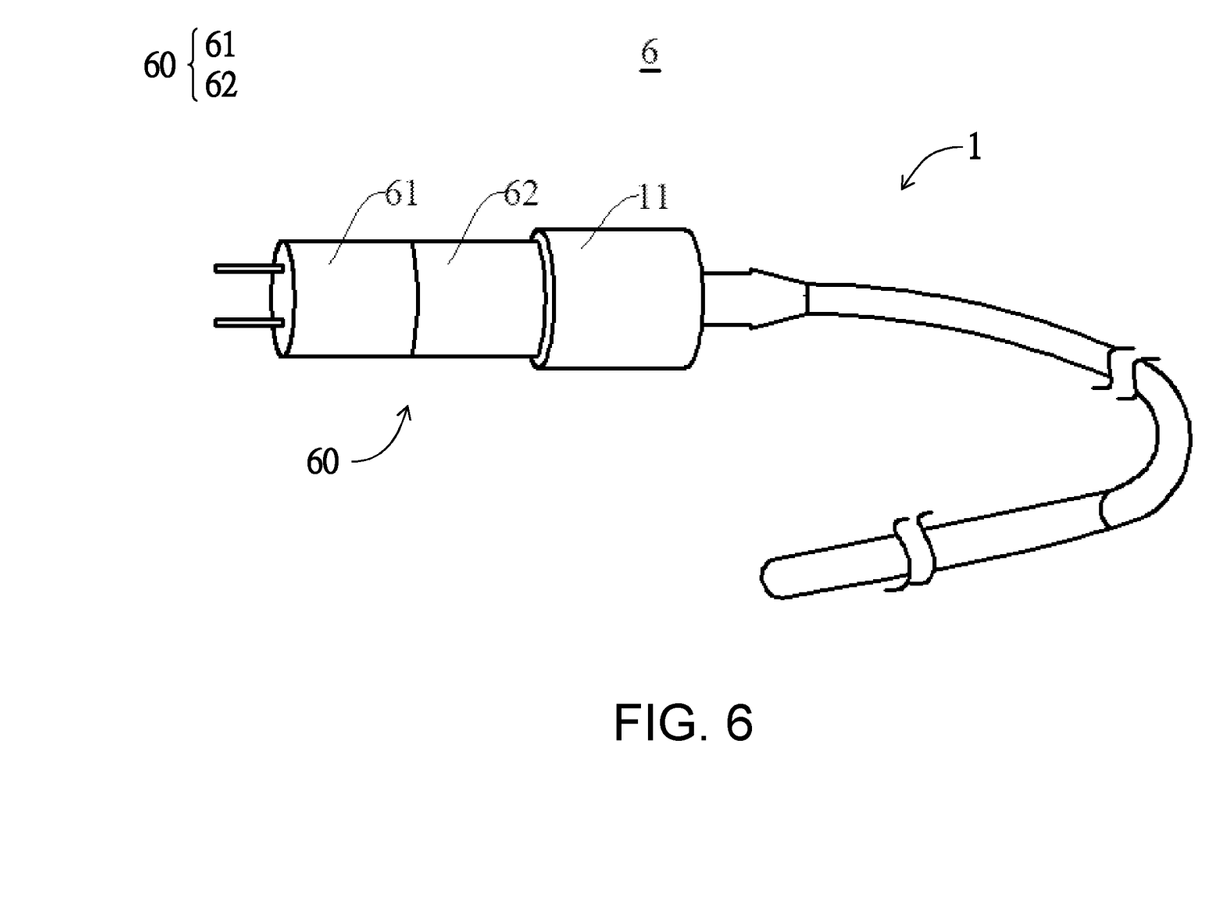
FIG. 6 is a structural view of a first ultrasonic probe of Embodiment 5 of the present invention.
Figure 7:
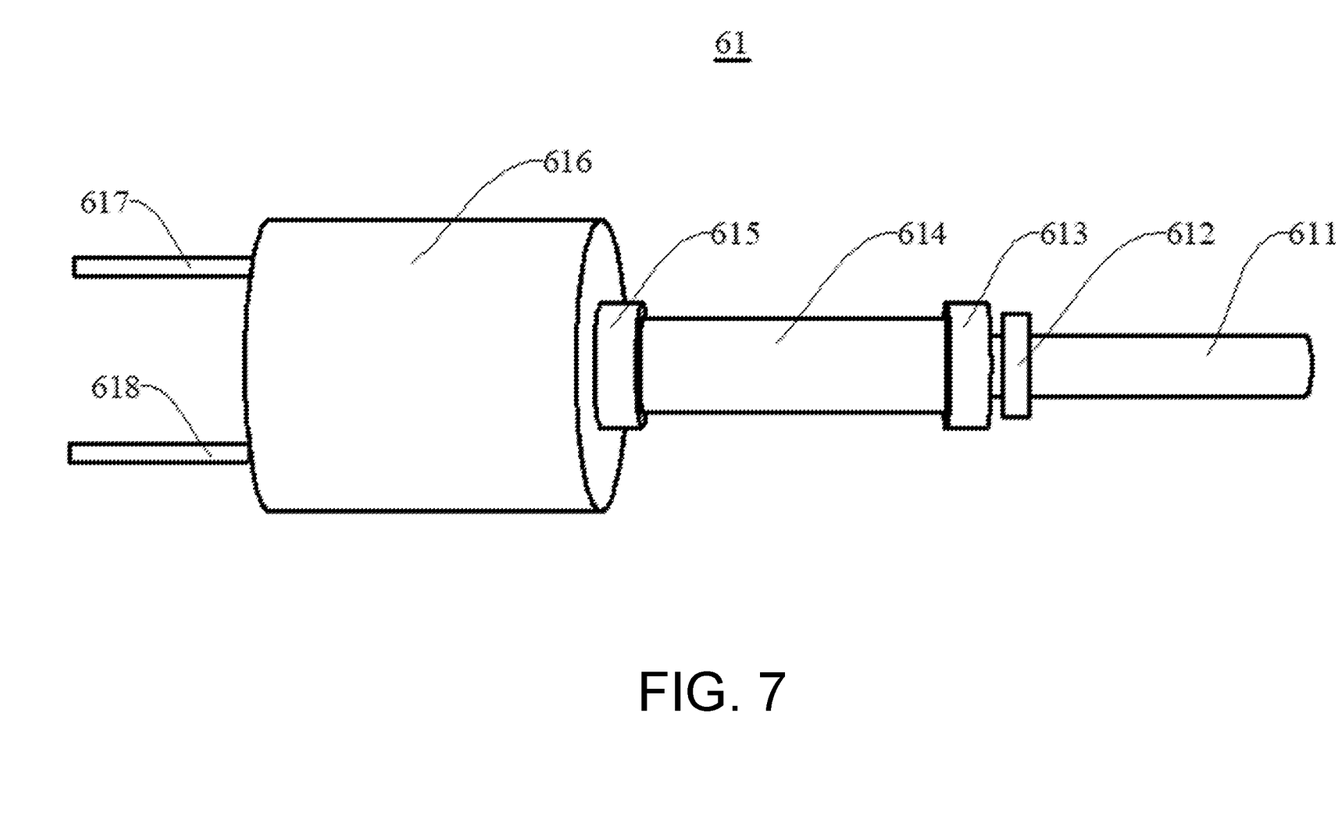
FIG. 7 is a structural view of a first socket portion shown in FIG. 6.
Figure 8:
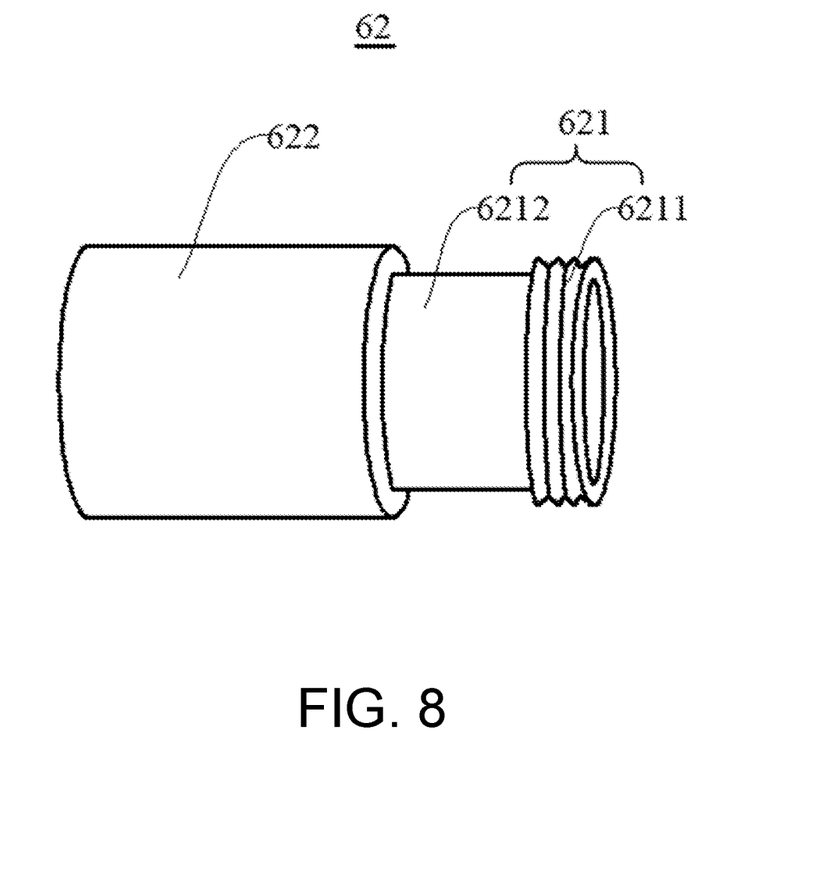
FIG. 8 is a structural view of a second socket portion shown in FIG. 6.
Figure 8A:
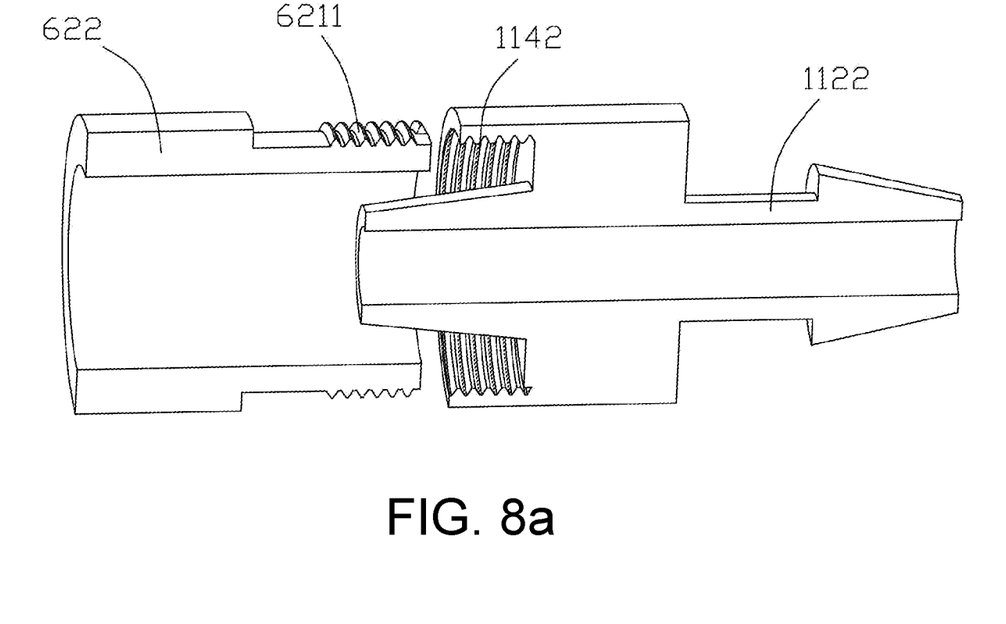
FIG. 8a and FIG. 8b are sectional views showing first threaded structure and second threaded structure are able to be engaged with each other.
Figure 8B:
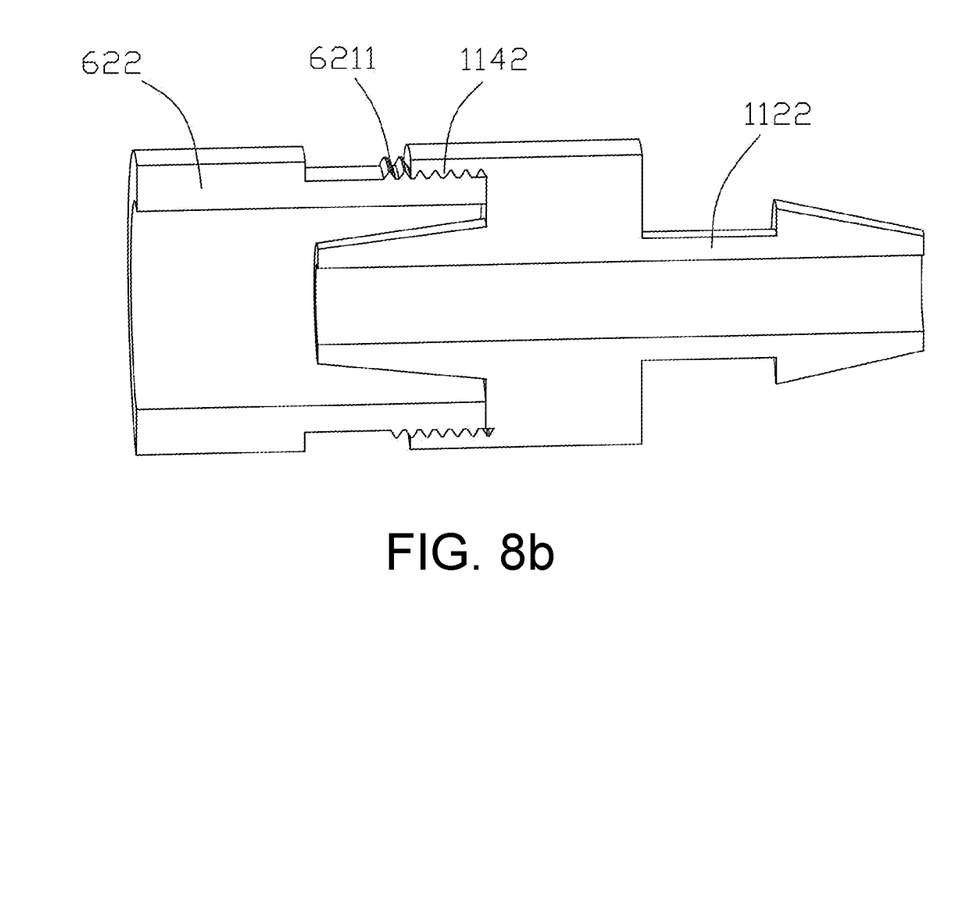

FIG. 6 is a structural view of a first ultrasonic probe of Embodiment 5 of the present invention. FIG. 7 is a structural view of a first connecting portion shown in FIG. 6. FIG. 8 is a structural view of a second connecting portion shown in FIG. 6.

With reference to FIGS. 1 and 6, the first ultrasonic probe 6 has a first connecting portion 61, a second connecting portion 62, and the first sheath assembly 1 which are sequentially connected. The second socket portion 62 is detachably and fixedly connected to the first plug portion 11.

With reference to FIG. 7, the first connecting portion 61 has a spring inner core 611, a bearing 613, a rotating portion 614, a sealing member 615 and a protective casing 616 which are sequentially connected and communicated with each other, and a first positioning pin 617 and a second positioning pin 618 disposed at a bottom portion of the protective casing 616. The structure of the first positioning pin 617 is the same as that of the second positioning pin 618. The sealing ring 612 is sleeved on an outer surface of the spring inner core 611. The inner diameter of the seal ring 612 is adapted to an outer diameter of the spring inner core 611, and the outer diameter of the seal ring 612 is smaller than the outer diameter of the bearing 613.

In the present embodiment, the first connecting portion 61 has a second inner diameter for receiving the torque transmitting portion, the second inner diameter being greater than or equal to 0.5 mm and larger than an outer diameter of the torque transmitting portion. With reference to FIG. 7, an inner diameter of the spring inner core 611 is the second inner diameter.

In some specific embodiments of the present invention, the second inner diameter is any one of 0.5 mm, 1.0 mm, 1.2 mm, and 1.4 mm.

In some embodiments of the present invention, the spring inner core 611, the bearing 613, the rotating portion 614, and the sealing member 615 have the same inner diameter.

With reference to FIGS. 2 and 8, the second connecting portion 62 has a second locking portion 621 and a butt joint portion 622 which are both in a hollow cylindrical structure and communicated with each other internally. A portion of the outer surface of the proximal end of the second locking portion 621 has a second threaded structure 6211. The first threaded structure 1142 and the second threaded structure 6211 may be engaged with each other, and the inner sidewall of the second locking portion 621 has a tapered structure, so as to receive the first locking portion 111 and is fitted to the outer sidewall of the first locking portion 111 by taper self-locking.

In some embodiments of the present invention, the first locking portion 111 is a hollow cylinder, and the inner diameter of the second locking portion 621 is adapted to the outer diameter of the first locking portion 111, so as to receive the first locking portion 111.

In some embodiments of the present invention, the inner diameter of the second locking portion 621 is 3 to 6 mm, and the length of the first locking portion 111 is equal to the length of the second locking portion 621.

With reference to FIGS. 7 and 8, the length of the second locking portion 621 is equal to a length of the spring inner core 611. The inner side wall of the butt joint portion 622 has an annular recess structure (not shown) which cooperates with the sealing ring 612, the bearing 613, the rotating portion 614 and the sealing member 615 to detachably and fixedly connect the first connecting portion 61 to the second connecting portion 62.

Figure 9:
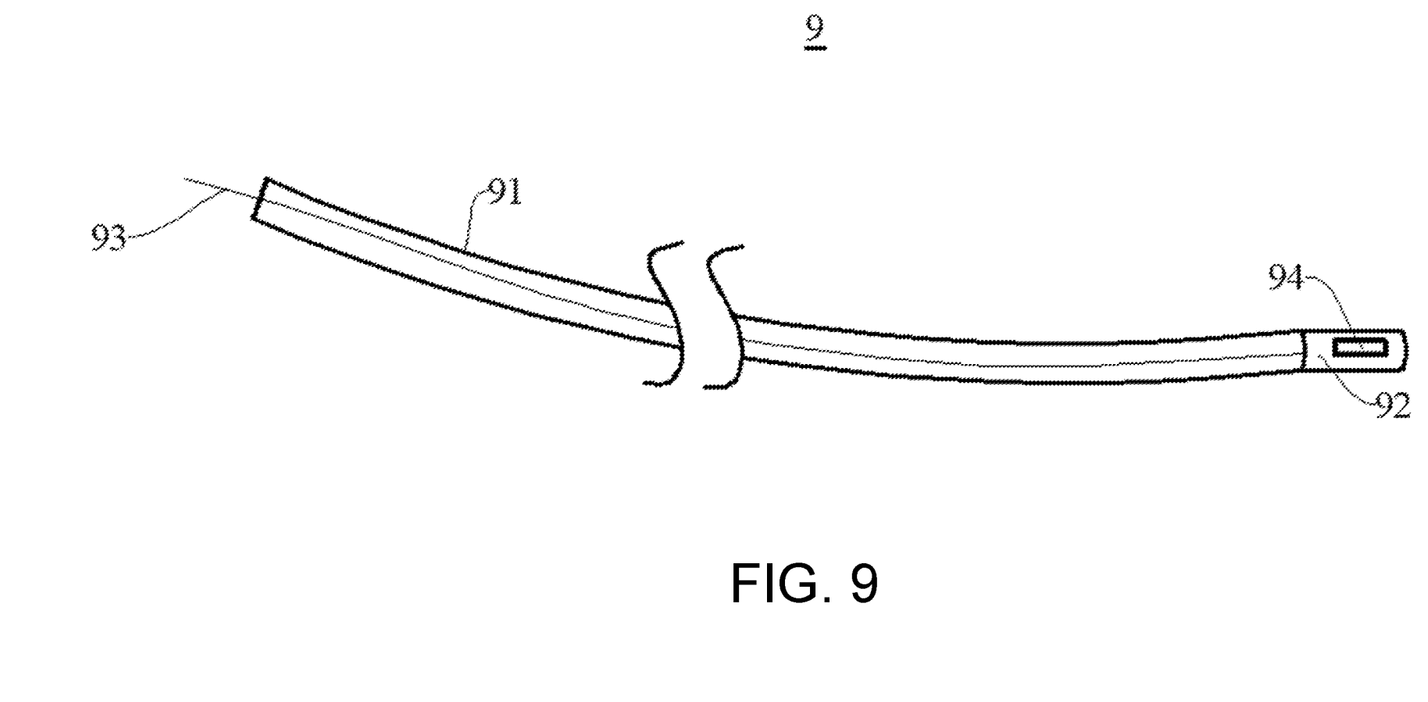
FIG. 9 is a structural view of a torque transmitting portion of Embodiment 5 of the present invention.

FIG. 9 is a structural view of a torque transmitting portion of Embodiment 5 of the present invention. With reference to FIG. 9, the torque transmitting portion 9 has a flexible sleeve 91, a metal protection tube 92, a coaxial cable 93, and an ultrasonic transducer 94. The flexible sleeve 91 is a hollow metal spiral tube structure, and the coaxial cable 93 passes through the inside of the flexible sleeve 91. One end of the metal protection tube 92 is fixed to the flexible sleeve 91 by welding, and a signal line (not shown) and a shield line (not shown) of the coaxial cable 93 are fixedly connected to the two electrodes (not shown) of the ultrasonic transducer 94 by soldering or bonding. One side of the metal protection tube 92 is provided with a mounting recess (not shown) for disposing the ultrasonic transducer 94.

With reference to FIGS. 1, 6 and 9, the fixed end of the torque transmitting portion 9 penetrates the spring inner core 611 and the bearing 613 to be fixed inside the rotating portion 614. The rotation of the rotating portion 614 drives the first positioning pin 617 and the second positioning pin 618 to rotate, so that the torque transmitting portion 9 transmits torque.

Embodiment 6

The present embodiment provides a second plug portion. The second plug portion has a main body portion, a third locking portion, and a second sheath connecting portion.

Figure 10:
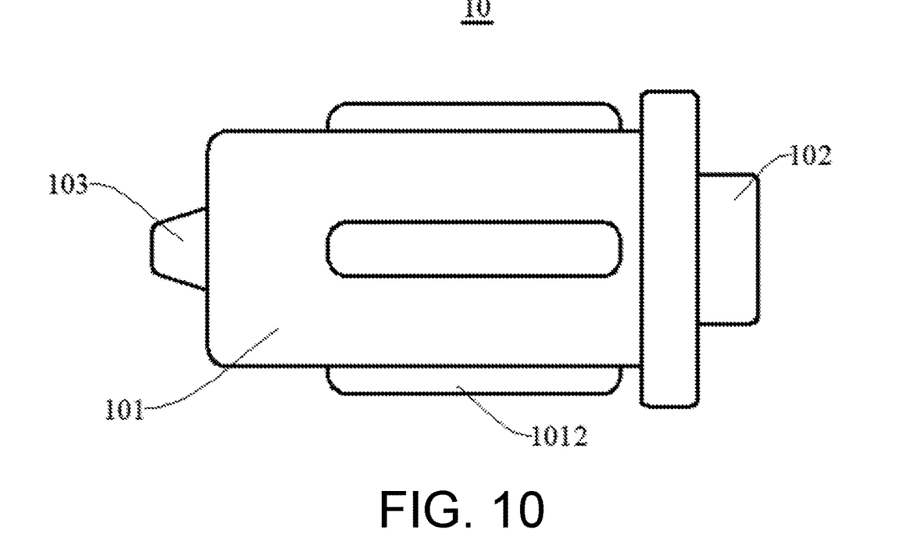
FIG. 10 is a structural view of a plug portion of Embodiment 6 of the present invention.
Figure 11:
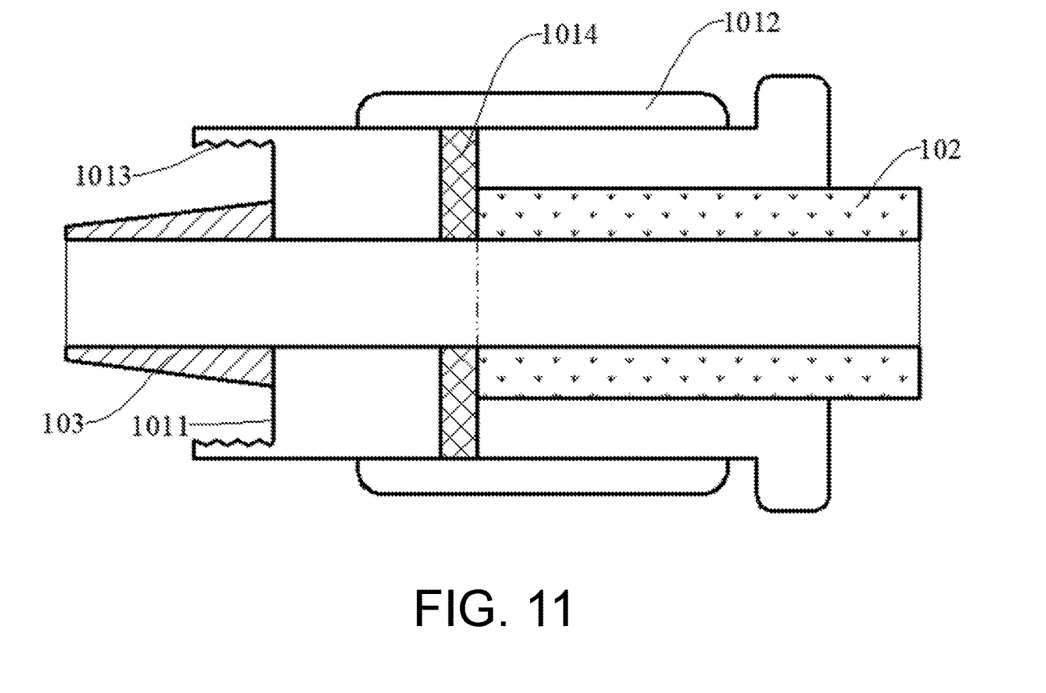
FIG. 11 is a longitudinal sectional view of the plug portion shown in FIG. 10.

FIG. 10 is a structural view of the second plug portion of the present embodiment. FIG. 11 is a longitudinal sectional view of the second plug portion shown in FIG. 10.

With reference to FIGS. 10 and 11, the second plug portion 10 has a main body portion 101, a second sheath connecting portion 102, and a third locking portion 103. A second recess 1011 is defined in one end of the main body portion 101, and the third locking portion 103 of a hollow structure is disposed at a bottom portion of the second recess 1011. A silicone sealing ring 1014 is fixed to the inside of the main body portion 101. An outer sidewall of the main body portion 101 has four anti-slip members 1012. An inner sidewall of the second recess 1011 is provided with a third threaded structure 1013. An inside of the main body portion 101 communicates with an inside of the second sheath connecting portion 102.

With reference to FIGS. 1, 8 and 11, a portion of the second sheath connecting portion 102 is received inside the main body portion 101, with one end being closely fitted to the silicone sealing ring 1014. One end of the first sheath 121 is fixed inside the second sheath connecting portion 102. On the one hand, the locking connection of the second locking portion 621 and the third locking portion 103 may be realized by rotating the main body portion 101 by holding the anti-slip members 1012. On the other hand, since a portion of an outer sidewall of the second sheath connecting portion 102 is closely fitted to a portion of an inner sidewall of the main body portion 101 and is rotatable relative to the main body portion 101, the second sheath connecting portion 102 may be prevented from rotating when the main body portion 101 rotates, thereby avoiding the problem that the first sheath 121 is twisted and deformed.

While the embodiments of the present invention have been described in detail, it will be apparent to those skilled in the art that various modifications and changes can be made to the embodiments. However, it is to be understood that such modifications and variations are within the scope and spirit of the present invention as described in the appended claims. Furthermore, the present invention described herein is susceptible to other embodiments and may be embodied or carried out in various ways.

What is claimed is:

1. An ultrasonic probe, comprising:
    a connecting butt joint portion;
    a torque transmitting portion; and
    a sheath assembly, including:
        a plug portion; and
        a sheath portion,
        wherein one end of the plug portion is used for detachably and fixedly connecting with the connecting butt joint portion;
        a sheath connecting portion of the plug portion is fixedly connected to one end of the sheath portion; and
        an inside of the plug portion communicates with an inside of the sheath portion to receive the torque transmitting portion,
    wherein the plug portion and the sheath portion of the sheath assembly are connected to each other;
    the connecting butt joint portion is detachably and fixedly connected to the plug portion; and
    a fixed end of the torque transmitting portion is fixedly connected in the connecting butt joint portion, and a transducer end of the torque transmitting portion extends through the connecting butt joint portion and the plug portion to enter the sheath portion,
    wherein the plug portion comprises a first locking portion and a fixing portion, one end of the fixing portion defines a recess, one end of the first locking portion is fixed to a bottom portion of the recess, and an inner sidewall of the recess has a first threaded structure to realize the detachably-fixed connection with the connecting butt joint portion through threaded engagement, and the first locking portion extends from the bottom portion of the recess and beyond an edge of the first threaded structure,
    the first locking portion has an internal hollow structure, an inside of the first locking portion communicates with an inside of the sheath portion, and the first threaded structure surrounds the first locking portion,
    the first locking portion is a truncated cone structure, and an outer sidewall of the first locking portion has a taper shape, such that the first locking portion is received inside the connecting butt joint portion and is fixedly connected to the connecting butt joint portion by taper self-locking.

2. The ultrasonic probe of claim 1, wherein the connecting butt joint portion has a first connecting portion, and the first connecting portion has a second inner diameter; the second inner diameter is used for receiving the torque transmitting portion, and the second inner diameter is greater than or equal to 0.5 mm and is larger than an outer diameter of the torque transmitting portion.

3. The ultrasonic probe of claim 2, wherein the connecting butt joint portion further has a second connecting portion, and the second connecting portion is coaxially connected to the first connecting portion in a detachably fixed connection manner; a portion of an outer surface of the second connecting portion has a second threaded structure for locking with the first threaded structure of the plug portion through threaded engagement.

4. The ultrasonic probe of claim 3, wherein the second connecting portion receives the first locking portion such that an inside of the connecting butt joint portion communicates with an inside of the sheath assembly, an inner sidewall of the second connecting portion being fitted to an outer sidewall of the first locking portion.

5. The ultrasonic probe of claim 4, wherein the inner sidewall of the second connecting portion has a taper to receive the first locking portion, and the second connecting portion is connected to the first locking portion by taper self-locking.

6. The ultrasonic probe of claim 4, wherein a Shore hardness of the first locking portion is less than that of the second connecting portion.

* * * * *

UNITED STATES PATENT AND TRADEMARK OFFICE
CERTIFICATE OF CORRECTION

PATENT NO. : 11,696,742 B2  
APPLICATION NO. : 16/611479  
DATED : July 11, 2023  
INVENTOR(S) : Changgeng Liu et al.

Page 1 of 1

It is certified that error appears in the above-identified patent and that said Letters Patent is hereby corrected as shown below:

On the Title Page

Item (73) Assignee's Name should read: Shengsuo Biotech (Shanghai) Corp. Ltd., Shanghai (CN)

Signed and Sealed this  
Fifth Day of September, 2023

Katherine Kelly Vidal  
*Director of the United States Patent and Trademark Office*